US008318976B2

(12) United States Patent
Heiman et al.

(10) Patent No.: US 8,318,976 B2
(45) Date of Patent: *Nov. 27, 2012

(54) SALTS, AQUEOUS LIQUID COMPOSITIONS CONTAINING SALTS OF S-(+)-ABSCISIC ACID AND METHODS OF THEIR PREPARATION

(75) Inventors: Daniel F. Heiman, Libertyville, IL (US); Bala Devisetty, Buffalo Grove, IL (US); Peter D. Petracek, Grayslake, IL (US); Xiaozhong Liu, Vernon Hills, IL (US); John Lopez, Gurnee, IL (US); Derek D. Woolard, Zion, IL (US); Yueh Wang, Arlington Heights, IL (US); Gregory D. Venburg, Deerfield, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1290 days.

This patent is subject to a terminal disclaimer.

(21) Appl. No.: 12/011,846

(22) Filed: Jan. 30, 2008

(65) Prior Publication Data

US 2008/0207454 A1 Aug. 28, 2008

Related U.S. Application Data

(60) Provisional application No. 60/898,550, filed on Jan. 31, 2007.

(51) Int. Cl.
*A01N 35/00* (2006.01)
*A01N 43/02* (2006.01)
*A01N 31/02* (2006.01)

(52) U.S. Cl. ......... 562/508; 504/348; 504/140; 504/162

(58) Field of Classification Search ..................... None
See application file for complete search history.

(56) References Cited

U.S. PATENT DOCUMENTS

| | | | |
|---|---|---|---|
| 4,209,530 A | 6/1980 | Visscher | |
| 4,434,180 A | 2/1984 | Visscher | |
| 5,201,931 A | 4/1993 | Abrams et al. | |
| 5,518,995 A | 5/1996 | Abrams et al. | |
| 6,004,905 A | 12/1999 | Abrams et al. | |
| 2004/0023938 A1 | 2/2004 | Tabuchi et al. | |
| 2004/0035162 A1 | 2/2004 | Williams et al. | |
| 2008/0196464 A1* | 8/2008 | Liu et al. | 71/59 |
| 2008/0227641 A1* | 9/2008 | Heiman et al. | 504/320 |
| 2008/0254986 A1* | 10/2008 | Silverman et al. | 504/140 |
| 2008/0254987 A1* | 10/2008 | Liu et al. | 504/142 |
| 2010/0152046 A1* | 6/2010 | Belkind et al. | 504/142 |

FOREIGN PATENT DOCUMENTS

| | | |
|---|---|---|
| GB | 1251867 | 11/1971 |
| JP | 2007 091611 | 4/2007 |

OTHER PUBLICATIONS

Roberts et al Journal of Organic Chemistry, 1968, 33, 3566-3569.*
Constantino et al Journal of Organic Chemistry 1989, 54, 681-683.*
Railton et al., "Effects of Abscisic Acid on the Levels of Endogenous Gibberellin-like Substances in Solanum Andigena", Plants (berl.) 112, 1973, pp. 65-69.
Blumenfeld et al., "Cuticular Penetration of Abscisic Acid", Planta (Berl.) 107, 1972, pp. 261-268.
Bonnafous et al., "Mouvelle Methode De Resolution Optique de L'Acide Abscisique", Tetrahedron Letters No. 13, 1973, pp. 1119-1122.
Yu et al., "Abscisic Acid Stimulates a Calcium-Dependent Protein Kinase in Grape Berry", Plant Physiology, vol. 140, Feb. 2006, pp. 558-579.
Kriedemann et al., "Abscisic Acid and Stomatal Regulation", Plant Physiology, 49, 1972, pp. 842-847.
Zeevart et al., "Metabolism and Physiology of Abscisic Acid", Ann. Rev. Plant Physiol Plant Mol. Biol., 39 1988, pp. 439-473.
Southwick et al., "A Rapid, Simple Synthesis and Purification of Abscisic Acid Glucose Ester", Plant Physiology 1986, 81 pp. 323-325.
Mauseth, "Botany an introduction to plant biology", 1991 Philadelphia Saundera pp. 348-415.
Raven et al Biology of plants fifth edition, 1992 New York Worth. pp. 545-572.
Milborrow, "The chemistry and physiology of abscisic acid", Am. Rev. Plant Physiol. 1974, 25 pp. 259-307.
Zhang et al., "Purification and identification of a 42-kilodalton abscisic acid-specific-binding protein from epidermis of broad bean leaves", Feb. 2002, Plant Physiology, vol. 128, pp. 714-725.
Finkelstein et al., "Abscisic Acid Biosynthesis and Response", 2002 The Arabidopsis Book, American Society of Plant Biologists, pp. 1-52.
EP Search Report issued Sep. 16, 2011.
Inomata et al., "The biosynthetic pathway to abscicis acid via ionylideneethane in the fungus botrytis cinerea", Phytochemistry, Pergamon Press, GB, col. 65, No. 19, Oct. 2004, pp. 2667-2678, XP004586634.
Abrams et al., "Ration of (S)- to (R)-abscisic acid from plant cell cultures supplied with racemic aba", Phytochemistry, Pergamon Press, GB, vol. 28, No. 11, Jan. 1, 1989, pp. 2885-2889, XP026620728.
Addicott et al., "Physiology of abscisic acid and related substances", Annu. Rev. Plant Physiol., vol. 20, 1969, pp. 139-164, XP007919384.

* cited by examiner

*Primary Examiner* — Yevegeny Valenrod
(74) *Attorney, Agent, or Firm* — Wood, Phillips, Katz, Clark & Mortimer

(57) ABSTRACT

The present invention generally relates to salts of S-(+)-abscisic acid, aqueous liquid compositions containing salts of S-(+)-abscisic acid and methods of their preparation for agricultural use.

4 Claims, No Drawings

SALTS, AQUEOUS LIQUID COMPOSITIONS CONTAINING SALTS OF S-(+)-ABSCISIC ACID AND METHODS OF THEIR PREPARATION

FIELD OF THE INVENTION

The present invention generally relates to salts of (S)-(+)-abscisic acid, aqueous liquid compositions containing salts of (S)-(+)-abscisic acid and methods of their preparation for agricultural use.

BACKGROUND OF THE INVENTION

Abscisic acid is a naturally occurring plant hormone which acts primarily to inhibit growth of plants, maintain dormancy of buds, inhibit fruit-ripening, activate the pathogen resistance response defense, induce senescence in already-damaged cells and their proximate neighbors, and help the plant tolerate stressful conditions. See Arteca, R. (1996), *Plant Growth Substances: Principles and Applications*. New York: Chapman & Hall; Mauseth, J. D. (1991), *Botany: An Introduction to Plant Biology*. Philadelphia: Saunders. pp. 348-415; Raven, P. H., Evert, R. F., and Eichhorn, S. E. (1992), *Biology of Plants*. New York: Worth. pp. 545-572.

Abscisic acid owes its name to the belief that this plant growth regulator causes the abscission of leaves from deciduous trees in the fall. Absicin II and dormin are names previously used for this plant hormone. The chemistry and physiology of abscisic acid and its analogs is described by Milborrow, Ann. Rev. Plant Physiol. 1974, 25, 259-307.

The naturally occurring enantiomeric form of abscisic acid is (S)-(+)-abscisic acid. In some literature reports the other enantiomer, (R)-(−)-abscisic acid is seen to be biologically inactive. In other research, it has been reported that (R)-(−)-abscisic acid also has some biological activities, however, they are often different from those of the (S)-(+)-enantiomer. See, Zeevart J. A. D. and Creelman, R. A. (1988) *Metabolism and Physiology of Abscisic Acid*, Annu. Rev. Plant Physiol. Plant Mol. Biol. 39, 439-473. Thus for use in a commercial agricultural product, the compositions of the present invention, comprising (S)-(+)-abscisic acid as the active ingredient are preferable to the prior art compositions comprising racemic (R,S)-(±)-abscisisc acid, since in the best case, half of the racemic material is inert, resulting in the need to purchase, formulate, package, ship and apply twice as much material, and potentially resulting in added undesirable residual material in food crops and additional environmental pollution. In the worst case, the (R)-(−)-enantiomer in racemic (R,S)-(±)-abscisisc acid can add undesirable side effects to the desired result produced by the applied (S)-(+)-abscisic acid in it.

The stereochemistry of the side chain of the major part of naturally occurring abscisic acid is 2-cis-,4-trans-, since that is the isomer that is produced biosynthetically by all green plants and some microorganisms. A smaller amount of the (S)-(+)-2-trans-,4-trans-isomer is also found to occur naturally, since it is produced photolytically by the action of sunlight on the (S)-(+)-2-cis-,4-trans-isomer. The (S)-(+)-2-trans-,4-trans-isomer is reported to be biologically inactive. See P. E. Kreidelmann, et al., Plant Physiol. 49, 842-847 (1972), D.-P. Zhang, et al., Plant Physiol. 128, 714-725, (2002) or X.-C. Yu, et al., Plant Physiol. 140, 558-579 (2006).

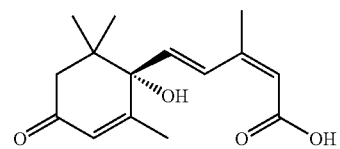

(S)-(+)-2-cis-,4-trans-abscisic acid

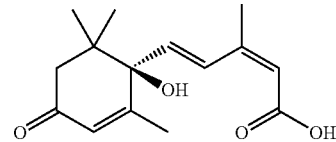

(R)-(−)-2-cis-,4-trans-abscisic acid

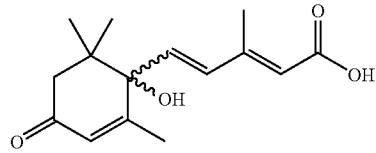

(R,S)-(±)-2-trans-,4-trans-abscisic acid

Prior art (U.K. Pat. No. 1251867 and Railton and Wareing, Planta 112, 65-69, 1973) teaches, inter alia, preparation of amine salts of racemic abscisic acid. A salt of racemic (R,S)-(±)-2-trans-,4-trans-abscisic acid with the chiral alkaloid brucine was prepared as a means of resolving a small quantity of the racemate in order to study the physical properties of its enantiomers (J. C. Bonnafous, et al., Tetrahedron Letters, 1119-1122, 1973). However, the prior art does not disclose salts of (S)-(+)-cis-,trans-abscisic acid with amines nor does it disclose alkali metal or alkaline earth salts of (S)-(+)-abscisic acid.

Gibberellic acids constitute a family of plant growth hormones similar to abscisic acid. Like abscisic acid, gibberellic acids are isoprenoids, arising biosynthetically from mevalonate via isopentenyl pyrophosphate (V. M. Sponsel, *The Biosynthesis and Metabolism of Gibberllins in Higher Plants*; D. C. Walton and Y. Li, *Abscisic Acid Biosynthesis and Metabolism*, both in *Plant Hormones Physiology, Biochemistry and Molecular Biology*, ed. P. J. Davies, Kluwer Academic Publishers, Dordrecht, 1995). Like abscisic acid, gibberellic acids possess a carboxylic acid functional group, as their names imply, and both gibberellic acids and abscisic acid consist of complex carbon- and oxygen-containing ring structures including carbon-carbon double bonds. In their natural function as plant hormones all of these compounds have relatively short lifetimes, since it is critical for the plants to be able to turn off rapidly the signals produced by any of these compounds, and thus chemical stability is not a necessary characteristic for their utility to the plant. Because of their beneficial plant hormonal activities several of the gibberellic acids (gibberellic acid A3, gibberellic acid A4 and gibberellic acid A7) have been commonly employed as agricultural products for many years (R. A. Menendez, 2000, Commercial uses of gibberellins in agriculture, Proceedings of the 27th Annual Meeting of the Plant Growth Regulation Society of America, 81-86). However, all commercial formulations of the gibberellic acids are either solid powders or granules or are solutions in various organic solvents. No aqueous solution formulations of any of the gibberellic acids are manufactured and sold because the gibberellic acids are unstable in water solution, and the concentration of active ingredient in the solution would gradually decrease so that the formulation would lose its efficacy over a period of a few weeks or months.

In light of the above information, it would be expected that solid powder or granule formulations or organic solvent solutions of abscisic acid would be the only forms acceptable for commerce, and that compositions comprising aqueous solutions of salts of abscisic acid would not exhibit sufficient stability for utility in ordinary practical use. However, we have unexpectedly found that either inorganic alkali metal or alkaline earth salts or organic amine salts of abscisic acid demonstrate good stability in either short-term elevated temperature testing or under storage at normal room temperature for long periods of time.

As noted above, abscisic acid is a carboxylic acid, and thus in a medium having an acidic pH, it is protonated and in its neutral undissociated form. This uncharged, undissociated form is more lipophilic than a salt of abscisic acid, and penetration of the uncharged acid form into the plant cuticle would be favored relative to the charged, dissociated form of abscisic acid present at higher pH (Blumenfeld and Bukovac 1972, Planta 107: 261-268). The uncharged, undissociated form of abscisic acid would be expected to cross cell membranes from the apoplast into the cytosol more easily than a salt form. In spite of this, we have surprisingly found that treatments comprising the salts of abscisic acid of the present invention perform equally well in biological activity when compared with similar treatments comprising the acid form of abscisic acid at the same concentration.

Abscisic acid was first defined in the early 1960s as a growth inhibitor accumulating in abscising cotton fruit and in leaves of sycamore trees photoperiodically induced to become dormant. See, Finkelstein R R, Rock C D (2002), *Abscisic Acid Biosynthesis and Response*, The Arabidopsis Book Vol. 45, No. 1 pp. 1-48. Since then, abscisic acid has been shown to regulate many aspects of plant growth and development, including embryo maturation, seed dormancy, germination, cell division and elongation, etc. Although abscisic acid has historically been thought of as a growth inhibitor, young tissues have high abscisic acid levels, and abscisic acid-deficient mutant plants are severely stunted because their ability to reduce transpiration and establish turgor is impaired. Exogenous abscisic acid treatment of mutants restores normal cell expansion and growth.

Abscisic acid is thought to initiate its effects on cells through binding to receptor proteins, although their identities and locations are still largely unknown. Activation of the putative receptor(s) causes a chain of events that results in rapid changes in ion channels and slower changes in the pattern of gene transcription. While many individual components of this chain of events have been identified, a complete picture has not yet been obtained.

Commercial formulations comprising abscisic acid are used in agriculture for various purposes, such as improving stress tolerance, slowing the growth rate, adjusting flowering phase, and other purposes. Abscisic acid has also been reported to possess insect inhibition qualities. See U.S. Pat. Nos. 4,434,180 and 4,209,530 to Visscher. Contents of these patents are herein incorporated by reference. Abscisic acid in a powdered form is currently commercially available from Lomon Biotechnology Company, Ltd., a Chinese company, which markets it as a substance that, among other uses, improves the yield and quality of certain crops.

However, one of the problems associated with prior art abscisic acid formulations is abscisic acid's relatively poor solubility in water: not more than about 3 grams per liter or alternatively, less than 0.3% by weight will dissolve at ordinary temperatures. A concentration of about 3000 parts per million (ppm) is the highest concentration that can be achieved in pure water at room temperature. Abscisic acid solubility in hard water is even less. While abscisic acid has better solubility in some organic solvents, liquid formulations of abscisic acid in organic solvents are unacceptable in some contexts because of flammability, toxicity or pollution considerations. For example, the Environmental Protection Agency of the U.S. state of California is currently requiring that liquid formulations of agricultural products contain no volatile organic solvent, and several other U.S. states are considering similar regulations. Nonvolatile organic solvents have the detriment that, since they do not evaporate, they remain in the agricultural product as it impinges upon and is absorbed into the target plant, with a probability of causing phytotoxicity and contaminating food products, since the amount of the solvent greatly exceeds the amount of active ingredient applied. Moreover, even in many organic solvents, the solubility of abscisic acid is too low to be of practical value. For example, abscisic acid is poorly soluble in propylene glycol, a relatively desirable solvent for agricultural formulations because of its low toxicity and high flash point.

A further problem observed with concentrated solutions of (S)-(+)-abscisic acid in organic solvents is that it is difficult to prepare more dilute solutions by dilution into water without having a portion of the (S)-(+)-abscisic acid precipitate out in a gummy form that redissolves only very slowly and with great difficulty. This is of practical importance because a major use of (S)-(+)-abscisic acid in agriculture or horticulture is for the reduction of transpiration in nursery plants being prepared for transplantation or for sale to consumers, for which purpose (S)-(+)-abscisic acid is often applied by means of an injection system and automatic or hand applicators. The solution for use in such an applicator must be a concentrate between about 50 and 100 times more concentrated than the dose rate that actually reaches the plants when they are treated by foliar spray or drench. Thus for a typical application to nursery plants of 60 to 600 ppm, the concentrate must contain between 3000 and 60,000 ppm of (S)-(+)-abscisic acid in a solution that will mix instantly and completely with the water flowing through the hose, in such a way that there is no possibility of formation of a precipitate that would clog the nozzle through which the water containing active ingredient is applied to the plants or the growing media of the plants. As explained above, the solubility of (S)-(+)-abscisic acid in water is not greater than 3000 ppm at ordinary ambient temperature, so such an intermediate solution cannot practically be prepared in water. A solution of (S)-(+)-abscisic acid in an organic solvent cannot be used in such an injection applicator, because precipitation of the active ingredient will occur during the mixing into the water flowing in the system, and the spray nozzle will be clogged. Because of the solubility limitation, it is also not possible to provide a liquid formulation of the (S)-(+)-abscisic acid in organic solvent at a higher concentration (e.g. 10%) and then at the time of application to prepare an intermediate dilution in water to achieve the desired concentration of 3,000 to 60,000 ppm in the reservoir of the injection applicator.

An identical problem arises in the case of application of (S)-(+)-abscisic acid to a vineyard, orchard or agricultural field through an irrigation system, a practice commonly known as chemigation. Again, such a system requires a concentrated solution of the active ingredient in a liquid solvent in such a form that the solution is instantly and completely miscible with a stream of water flowing through the irrigation system. If any precipitation were to occur, it would block the nozzles (known as emitters) through which the water and dissolved active ingredient reach the target plants. Again in this situation a formulation consisting of an organic solution of (S)-(+)-abscisic acid would not be acceptable because of the problem of low water solubility.

While powdered formulations of abscisic acid are available, it is often more convenient to use concentrated liquid solutions instead of powders. Therefore, there is an unmet need in the art for abscisic acid formulations comprising salts of (S)-(+)-abscisic acid which are much more soluble in water than the acid itself.

SUMMARY OF THE INVENTION

The present invention is generally directed to salts of (S)-(+)-abscisic acid.

In a further embodiment, the present invention is generally directed to aqueous compositions comprising an effective amount of a salt of (S)-(+)-abscisic acid wherein the concentration of the salt is at least 0.5% by weight of the aqueous composition. Applicants have unexpectedly discovered that salts of (S)-(+)-abscisic acid allow for dramatic increases in solubility of (S)-(+)-abscisic acid in water so that concentrated solutions of abscisic acid can be obtained. As a result, solutions can be obtained with (S)-(+)-abscisic acid concentrations as high as 50% by weight. The present invention allows for the creation of concentrated formulations of (S)-(+)-abscisic acid that are convenient for packaging, storage, transport and handling, but must be diluted prior to use and specifically allows any arbitrary intermediate dilution of these formulations to be made into water without the risk of precipitation of the active ingredient.

Compositions of the present invention generally comprise the salt, an antimicrobial and a surfactant. Other components which enhance the long-term storage stability or the biological activity of the (S)-(+)-abscisic acid may optionally be included.

Some of the suitable salts of the invention include, but are not limited to, the ammonium salt, the lithium, sodium, potassium, magnesium, or calcium salts, organic amine salts or mixtures comprising any number of these. In one embodiment, the organic amine salt is the triethanolamine salt. In another embodiment, the organic amine salt is the dimethylethanolamine salt. In yet another embodiment, the organic amine salt is the ethanolamine salt. These examples of salts are not limiting as other salts may also be suitable for use the present invention. One presently preferred salt is the ammonium salt.

The present invention is also directed to methods of preparation of aqueous compositions comprising salts of (S)-(+)-abscisic acid. In one embodiment, the invention is directed to a method of preparation of the ammonium salt of abscisic acid comprising reacting (S)-(+)-abscisic acid with a chemically equivalent amount of ammonia in aqueous solution. In another embodiment, the invention is directed to a method of preparation of the lithium salt comprising reacting (S)-(+)-abscisic acid with lithium hydroxide, lithium bicarbonate or lithium carbonate in aqueous solution. In another embodiment, the invention is directed to a method of preparation of the sodium salt comprising reacting (S)-(+)-abscisic acid with a chemically equivalent amount of sodium hydroxide, sodium bicarbonate or sodium carbonate in aqueous solution. In another embodiment, the invention is directed to a method of preparation of the potassium salt comprising reacting (S)-(+)-abscisic acid with a chemically equivalent amount of potassium hydroxide, potassium bicarbonate or potassium carbonate in aqueous solution. In another embodiment, the invention is directed to a method of preparation of the magnesium salt comprising reacting (S)-(+)-abscisic acid with one-half to one chemical equivalent of magnesium hydroxide, magnesium oxide or magnesium carbonate or a hydrate thereof in aqueous solution or suspension. In another embodiment, the invention is directed to a method of preparation of the calcium salt comprising reacting (S)-(+)-abscisic acid with one-half to one chemical equivalent of calcium hydroxide, calcium oxide or calcium carbonate in aqueous solution or suspension. In yet another embodiment, the invention is directed to a method of preparation of the organic amine salt comprising reacting (S)-(+)-abscisic acid with one chemical equivalent of an organic amine in the presence or, if the amine is a liquid, in the absence of water.

A further embodiment of the invention includes mixtures comprising combinations of salts of S-(+)-abscisic acid with an effective amount of a component or multiple components that enhance the long-term chemical stability of the (S)-(+)-abscisic acid and the mixture as a whole. Such components include but are not limited to citric acid or one of its water-soluble salts, sulfur dioxide or a water soluble bisulfite or sulfite salt.

A further embodiment of the invention includes mixtures comprising combinations of salts of S-(+)-abscisic acid with a substantial amount of a component or multiple components which enhance the biological activity of the (S)-(+)-abscisic acid, including but not limited to urea, ammonium nitrate, ammonium acetate, calcium chloride, magnesium nitrate or a surfactant. Preferred surfactants are gel-forming constituents, such as members of the Brij family.

A presently preferred embodiment of the present invention is an aqueous composition that comprises from about 5 to about 45 weight % of (S)-+)-abscisic acid as the ammonium salt and from about 0.1 to about 0.5 weight % potassium sorbate.

Another presently preferred embodiment of the present invention is an aqueous composition that comprises from about 5 to about 45 weight % of (S)-(+)-abscisic acid as the ammonium or potassium salt; from 0 to about 0.5 weight % potassium sorbate; from about 0.2 to about 1.0 weights % sodium citrate; and from about 0.1 to about 0.5 weight % sodium sulfite.

The disclosed embodiments are simply exemplary embodiments of the inventive concepts disclosed herein and should not be considered as limiting, unless the claims expressly state otherwise.

DETAILED DESCRIPTION OF THE INVENTION

The present invention relates to aqueous liquid compositions of salts of (S)-(+)-abscisic acid. Abscisic acid is an optically active 15-carbon carboxylic acid. The structural formula of 2-cis-, 4-trans-(S)-(+)-abscisic acid is set forth below:

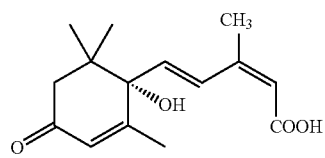

The liquid compositions of the present invention utilize the (S)-(+)-enantiomer and the 2-cis-,4-trans-stereochemistry of the carbon chain rather than a racemic mixture of enantiomers and any of the other possible combinations of stereochemistry of the carbon chain. Unless expressly stated otherwise, in all instances when the application refers to abscisic acid or (S)-(+)-abscisic acid, it refers specifically to 2-cis-,4-trans-(S)-(+)-abscisic acid.

In one aspect, the present invention relates to an aqueous composition for the treatment of plants comprising an effective amount of at least one salt of (S)-(+)-abscisic acid, wherein the concentration of the salt is at least 0.5% by weight of said salt.

As used herein, all numerical values relating to amounts, weight percentages and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The phrase "effective amount" of a salt means a sufficient amount of the salt to provide the desired biological or chemical effect without at the same time causing additional toxic effects. The amount of salt or other formulation component that is "effective" will vary from composition to composition, depending on the particular agricultural use, the particular salt or salts, and the like. Thus, it is not always possible to specify an exact "effective amount." However, an appropriate "effective amount" in any individual case may be determined by one of ordinary skill in the art using routine experimentation.

Liquid compositions of the present invention can be prepared as either ready-to-use dilutions or dilutable concentrates. According to the present invention, a solution containing from 0.5% to as much as 50% by weight of abscisic acid can be obtained. The dilutable concentrates can be diluted into water directly to a final application concentration or to any intermediate dilution, without risk of precipitation of the active ingredient. The aqueous formulations according to the present invention are inexpensive to manufacture, safe to handle and use, and the (S)-(+)-abscisic acid active ingredient is stable under storage and shipping conditions. With the compositions of the present invention there is no risk of fire as there might be with liquid formulations containing a flammable or combustible organic solvent. There is no risk of contributing to the formation of atmospheric pollution or smog as there is with formulations containing a volatile organic solvent. The aqueous formulations of the present invention are less toxic to humans or animals than similar formulations containing an organic solvent. A person having ordinary skill in the art would be able to determine how to prepare the final aqueous solution concentration for direct application to plants, or how to prepare any intermediate dilutions for use in chemigation equipment or injection diluters or similar equipment, without undue experimentation, without any chance of causing precipitation of the active ingredient and without long and laborious stirring to bring the active ingredient into solution.

The aqueous solution formulations of the present invention may also optionally include an effective amount of an additional ingredient or several additional ingredients in order to enhance the long-term chemical stability of the (S)-(+)-abscisic acid or the formulation as a whole. Such enhancing ingredients include but are not limited to citric acid or one of its water-soluble salts, sulfur dioxide or a water soluble bisulfite or sulfite salt. The use of water as the solvent allows for a combined liquid formulation comprising any or several of these inorganic components that may comprise a level of the enhancing ingredient equal to the concentration of the (S)-(+)-abscisic acid salt or higher, if desired.

The aqueous solution formulations of the present invention may also optionally include a substantial amount of an additional ingredient or several additional ingredients in order to enhance the biological activity of the (S)-(+)-abscisic acid. Such enhancing ingredients include but are not limited to urea, ammonium nitrate, ammonium acetate, calcium chloride and magnesium nitrate. The use of water as the solvent allows for a combined liquid formulation comprising any or several of these inorganic components or urea that may comprise a level of the enhancing ingredient equal to the concentration of the (S)-(+)-abscisic acid salt or even up to 10 times the amount of (S)-(+)-abscisic acid by weight or more. Again, this provides an advantage over the use of an organic solvent, in which these inorganic components or urea have little if any solubility.

Additionally, the aqueous solution formulations of the present invention may optionally include a substantial amount of a surfactant, in an amount equal by weight to the content of (S)-(+)-abscisic acid salt or even several times greater. Examples of surfactants that may be included in the compositions of the present invention include, but are not limited to products of the Brij family of polyoxyethylene fatty alcohol ethers (available from Uniquema, Castle Del.), products of the Tween family of polyoxyethylene sorbitan esters (available from Uniquema, Castle Del.), products of the Silwet family of organosilicones (available from Union Carbide, Lisle Ill.), products of the Triton family of alkylphenol ethoxylates (available from Dow Chemical Company, Midland Mich.), products of the Tomadol family of ethoxylated linear alcohols (available from Tomah3 Products, Inc., Milton Wis.), products of the Myrj family of polyoxyethylene fatty acid esters (available from Uniquema Castle Del.), products of the Trylox family of ethoxylated sorbitol and ethoxylated sorbitol esters (available from Cognis Corporation, Cincinnati Ohio), or any of the specific commercial products Latron B-1956 (available from Rohm & Haas, Philadelphia Pa.), Capsil (available from Aquatrols, Paulsboro N.J.), Agral 90 (available from Norac Concepts, Inc., Orleans ON, Canada), Kinetic (available from Setre, Memphis Tenn.), or Regulaid (available from KALO, Overland Park Kans.). The presently preferred surfactants are those of the Brij or Tween families. The most preferred surfactants for inclusion in compositions of the present invention are Brij 98, Brij 78, Tween 20 and Tween 40. The concentration of surfactant in the compositions of the invention may range from about 0.02% up to about 40% by weight. The preferred range of concentrations for the surfactant in the compositions of the invention is from about 0.1% to 30% by weight. The most preferred range of concentrations for the surfactant in the compositions of the invention is from about 0.25% to about 25% by weight. The surfactant may be included in the compositions of the present invention either together with any one or more of the inorganic salt or urea activity enhancing ingredients or in the absence of any of them.

The end user can apply compositions of the present invention to plants for various purposes, such as improving stress tolerance, reducing their water utilization, slowing their growth rate, adjusting flowering phase, for seed treatment, preventing preharvest fruit and flower drop and improving the quality and color of fruits. The possible uses may also include, for example, distribution and sale of various concentrated solutions of (S)-(+)-abscisic acid. Utilizing such high concentrations for shipping and handling allows the use of smaller volumes of water, thus simplifying shipping and handling procedures and decreasing costs. The end user could then dilute the product to a 1% concentration (or other percentage depending on the end user's needs) and fill the supply reservoir of mixing equipment for spray or drench application to ornamental bedding plants ready for shipment. Alternatively, another end user could prepare a diluted solution for injection into the drip irrigation system for a vineyard at the appropriate time to enhance the color or phenolic content of a wine or table grape crop.

Organic amine compounds that may be employed in the salts useful in the compositions of the present invention are those containing one or two nitrogen atoms. If the amine compound contains one nitrogen atom, it may include from one to six carbon atoms, from zero to three oxygen atoms and zero to four degrees of unsaturation, where a degree of unsaturation is defined as a carbon-carbon multiple bond or a ring in a cyclic structure. If the amine compound contains two nitrogen atoms, it may include from two to ten carbons, zero to four oxygen atoms and zero to four degrees of unsaturation. These organic amine compounds include, but are not limited to methylamine, ethylamine, propylamine, isopropylamine, dimethylamine, diethylamine, trimethylamine, triethylamime, ethanolamine, N-methylethanolamine, N,N-dimethylethanolamine, diethanolamine, triethanolamine, ethylenediamine, tetramethylethylenediamine, and other similar compounds.

In another aspect, the present invention relates to methods of preparation of the aqueous compositions comprising salts of (S)-(+)-abscisic acid. For example, in one embodiment, the invention is directed to a method of preparation of the ammonium salt of abscisic acid comprising reacting (S)-(+)-abscisic acid with ammonia. In another embodiment, the invention is directed to a method of preparation of the potassium salt comprising reacting S-(+)-abscisic acid with potassium hydroxide. In yet another embodiment, the invention is directed to a method of preparation of the organic amine salt comprising reacting (S)-(+)-abscisic acid with the organic amine.

In a preferred embodiment, at least about 0.25% by weight of Tween-20, a detergent polysorbate, is added to the reaction mixture and resulting formulation when preparing the (S)-(+)-abscisic acid salts.

In another preferred embodiment, the aqueous solution comprises an antimicrobial agent to prevent microbial growth during long-term storage. The presently most preferred antimicrobial agent is potassium sorbate. When the aqueous solution of an (S)-(+)-abscisic acid salt of the present invention is intended for long term storage or for distribution and commercial sale to the user, it is advantageous to incorporate the antimicrobial agent at a concentration of from about 0.01% to about 1.0% by weight.

In another preferred embodiment, the aqueous solution comprises an agent to prevent undesirable development of coloration or appearance of precipitate during long-term storage. The presently most preferred agents for this purpose are sodium or potassium citrate and sodium or potassium sulfite or bisulfite.

In the preferred embodiments, the pH of the concentrated compositions of the invention and any aqueous solutions at final use dilution prepared from the concentrates are both approximately neutral (near pH 7).

Preferred compositions of the present invention comprise from 0.5 to 50 weight % of (S)-(+)-abscisic acid in the form of a salt, from 0.01 to 1.0 weight % of an antimicrobial agent, optionally from about 0.01 to about 5 weight % of a stability enhancing agent, optionally from 0.25 to 35 weight % of a surfactant, optionally from about 1 to about 50 weight % of another activity enhancing component, with the balance being water.

The following examples are intended to illustrate the present invention and to teach one of ordinary skill in the art how to make and use the invention. They are not intended to limit the invention or its protection in any way.

EXAMPLES

Example 1

Preparation of an Aqueous Solution Composition of the Triethanolamine Salt of (S)-(+)-Abscisic Acid Triethanolamine (1.33 mL) and 2.64 g of (S)-(+)-abscisic acid of 95% nominal purity were dissolved in 50 mL of deionized water over approximately half an hour with good stirring. As a result, a water-clear, colorless solution was produced containing about 5% abscisic acid by weight. The pH of the solution was measured to be 6.3. The solution was frozen and lyophilized overnight. On the next day, a clear oil residue was present; the residue appeared to be fairly viscous. After adding a small amount of water a homogenous solution was obtained with a final volume of 7.5 mL or about 33% abscisic acid by weight in water in the form of the triethanolamine salt.

Then, water was added to bring the final volume to 25 mL in a graduated cylinder, resulting in a 10% by weight solution (based on the nominal purity of 95% for the abscisic acid). The solution was stored in a refrigerator over the weekend to test for stability against crystallization. After four days in a cold refrigerator (temperature between 0.5 to 3° C.), there was no evidence of crystallization. After three months at ambient temperature, the mixture was still water-clear.

The triethanolamine salt of (S)-(+)-abscisic acid allows preparation of a solution which has a very high (S)-(+)-abscisic acid salt concentration.

Example 2

Preparation of an Aqueous Solution Composition of the Dimethylethanolamine Salt of (S)-(+)-Abscisic acid 891 mg of dimethylethanolamine, MW 89.14 g/mol was dissolved in 5 mL of water. 100 mg of Tween-20 was added to the mixture. Then, 2.64 g of (S)-(+)-abscisic acid of 95% purity was added over the course of 2 to 3 minutes. The abscisic acid wetted and dissolved almost immediately, so that within five minutes, only a very few abscisic acid particles remained undissolved. An aqueous solution composition containing about 25% (S)-(+)-abscisic acid by weight in the form of the dimethylethanolamine salt was prepared.

Four 0.5 ml aliquots were prepared for assay and stability testing. The formulation passed the accelerated stability test; that is, the (S)-(+)-abscisic acid content remained unchanged during storage at about 55° C. over the course of two weeks. Passing this accelerated stability test is normally predictive that a composition will be stable a normal room temperature for at least two years. The control sample stored in a refrigerator in the dark was essentially unchanged in its appearance and (S)-(+)-abscisic acid content after two months in the cold.

An aqueous solution composition comprising 25% abscisic acid by weight as the dimethylethanolamine salt which can be stored without loss of active ingredient content for a long period of time was prepared.

Example 3

Preparation of an Aqueous Solution Composition of the Ethanolamine Salt of (S)-(+)-Abscisic Acid 610 mg of ethanolamine, MW 61.08 g/mol, together with 100 mg of Tween-20 were dissolved in 5 mL of water. 2.64 g of (S)-(+)-abscisic acid was added over the course of 2 to 3 minutes. The abscisic acid dissolved rapidly. The reaction was mildly exothermic as the temperature raised spontaneously from room temperature to about 35° C. A nearly colorless solution was produced. The volume was brought up to about 10 mL by adding a small volume of water. Therefore, Applicants were able to achieve an aqueous solution composition containing about 25% (S)-(+)-abscisic acid by weight in the form of the ethanolamine salt.

After the solution had been stored in a refrigerator for several hours, no change was observed. Four 0.5 mL aliquots were prepared for assay and stability testing. The formulation successfully passed accelerated stability testing, as described in the previous Example. The abscisic acid content remained unchanged throughout the testing.

An aqueous solution composition comprising 25% abscisic acid by weight in the form of the ethanolamine salt, which can be stored without loss of abscisic acid content for a long period of time was prepared.

Example 4

Preparation of an Aqueous Solution Composition of the Ammonium Salt of (S)-(+)-Abscisic Acid 5.28 g of (S)-(+)-abscisic acid were combined with 20 ml of water and dissolved by addition of 1.28 mL of concentrated ammonia solution. In about 10 minutes, the solid was all dissolved. During this time, 2 more drops of concentrated ammonia were added. The mixture was diluted to 50 mL with water in a volumetric flask (resulting in a 10% by weight solution) and was stored in a brown glass bottle. The pH of the aqueous solution composition was 8.0.

An aqueous solution composition comprising 10% (S)-(+)-abscisic acid by weight in the form of the ammonium salt was prepared.

Example 5

A. Preparation of an Aqueous Solution Composition of the Ammonium Salt of (S)-(+)-Abscisic Acid Comprising Potassium Sorbate In a 600 mL beaker, 55 g of (S)-(+)-abscisic acid of 95% purity was added, followed by 500 μL of Tween 20 and 200 mL of water. Then, 10 mL of concentrated aqueous ammonia were added while stirring until the mixture came to equilibrium. Then, additional concentrated ammonia was added dropwise until all solid was dissolved. A homogenous solution was achieved when a total of about 13.5 mL of ammonia has been added. At this point, potassium sorbate (1.25 g) was added to the composition; it quickly dissolved. The mixture was transferred to a 500 ml volumetric flask and was brought up to 500 mL with deionized water. The mixture was stored in a brown glass bottle. The pH was measured to be 6.50.

An aqueous solution composition comprising 10% abscisic acid as the ammonium salt by weight and further comprising a naturally-occurring antimicrobial preservative was prepared.

B. Stability of the Aqueous Solution Composition of the Ammonium Salt of (S)-(+)-Abscisic Acid to Low-Temperature Conditions A sample of the 10% aqueous solution composition of the ammonium salt of abscisic acid containing 0.25% potassium sorbate was stored in a freezer at −15° C. overnight. When recovered, the sample appeared frozen; however, when returned to normal room temperature, the sample melted to become a completely homogeneous solution, without any evidence of separation of undissolved solid. The sample was then stored in a freezer at −75° C. overnight. Again the sample appeared frozen; however, when returned to normal room temperature, the sample melted to become a completely homogeneous solution, without any evidence of separation of undissolved solid. When analyzed by HPLC, a result of 10.3% (S)-(+)-abscisic acid was obtained for both the sample that had been subjected to freezing and thawing and for a control sample that had been stored at normal room temperature (20-25° C.).

It was demonstrated that the aqueous solution composition comprising the ammonium salt of (S)-(+)-abscisic acid and potassium sorbate antimicrobial preservative is stable against exposure to low temperatures.

Example 6

A. Preparation of an Aqueous Solution Composition of the Potassium Salt of (S)-(+)-Abscisic Acid Comprising Potassium Sorbate 125 mg of potassium sorbate was added with 50 mg of Tween 20 into a 150 mL beaker. Then, 20 mL of water was added and 1.5 mL of 10M KOH, followed by 5.28 g of (S)-(+)-abscisic acid of 95% purity. After the mixture was stirred until no more abscisic acid was dissolving, the solution was titrated with 1.0M KOH. When all of the solid was finally dissolved, it was then transferred to a 50 mL volumetric task and appropriate amount of deionized water was added to bring the level to the 50 mL mark. Then, the solution was stored in a brown glass bottle. The pH was measured to be around 6.30.

An aqueous solution composition comprising 10% abscisic acid by weight as the potassium salt and additionally comprising a naturally-occurring antimicrobial preservative was prepared.

B. Storage Stability of the Aqueous Solution Compositions of the Potassium Salt of (S)-(+)-Abscisic Acid with or without Antimicrobial Preservative A sample of the 10% aqueous solution composition of the potassium salt of abscisic acid containing no potassium sorbate was stored at normal room temperature (20 to 25° C.) and assayed for abscisic acid content by HPLC at 13 and again at 15 months. Concentrations found were 10.4% and 10.2% respectively, both matching the expected value to within the uncertainty of the assay methodology.

A sample of the 10% aqueous solution composition of the potassium salt of abscisic acid containing 0.25% potassium sorbate antimicrobial preservative was stored at normal room temperature (20 to 25° C.) and assayed for abscisic acid content after 10 and one half months. The abscisic acid content was found to be 10.1%.

It was demonstrated that the presence of the potassium sorbate antimicrobial preservative exhibited no detrimental effect on the chemical stability of the abscisic acid active ingredient.

Example 7

Preparation of an Aqueous Solution Composition of the Lithium Salt of (S)-(+)-Abscisic Acid When 2.64 g of 95% pure (S)-(+)-abscisic acid was stirred in 10 mL of water containing 25 microL of Tween 20, a white suspension was quickly formed. A solution of 420 mg of lithium hydroxide monohydrate (41.96 g/mol) in 10 mL of water was added with stirring over the course of a few minutes, causing all the abscisic acid to dissolve and producing a clear solution of pH 6.89. As an antimicrobial preservative, 63 mg of potassium sorbate was added, and that also quickly dissolved. The solution was transferred to a graduated cylinder and made up to exactly 25 mL by addition of deionized water A 10% abscisic acid by weight solution in water as the lithium salt of (S)-(+)-abscisic acid comprising a naturally-occurring preservative was prepared.

Example 8

Preparation of an Aqueous Solution Composition of the Sodium Salt of (S)-(+)-Abscisic Acid A suspension of 2.64 g of (S)-(+)-abscisic acid (95% purity) in 10 mL of water containing 25 mg of Tween 20 was stirred gently while adding 9.5 mL of 1.0 M aqueous sodium hydroxide. Most of the abscisic acid dissolved during the addition. The solution was titrated to pH 7.4 by addition of a few additional drops of sodium hydroxide solution, and this brought the remaining abscisic acid into solution. Potassium sorbate (63 mg) was added as an antimicrobial and dissolved with stirring. The solution was made up to 25 mL final volume by addition of deionized water.

A 10% abscisic acid by weight solution in water as the sodium salt comprising a naturally-occurring preservative was prepared.

Example 9

Preparation of an Aqueous Solution Composition of the Magnesium Salt of (S)-(+)-Abscisic Acid A suspension of 2.64 g of (S)-(+)-abscisic acid (95% purity) and 403 mg of magnesium oxide (10 mmoles) in 20 mL of deionized water containing 50 microL of Tween 20 was stirred in a sealed container for one week. The resulting suspension was diluted to 50 mL by addition of deionized water and filtered. Potassium sorbate (63 mg) was added as an antimicrobial preservative, and the solution was swirled by hand to dissolve it. Assay by HPLC showed the solution to contain 4.0% (S)-(+)-abscisic acid by weight as the magnesium salt.

Example 10

Preparation of an Aqueous Solution Composition of the Calcium Salt of (S)-(+)-Abscisic Acid A suspension of 2.64 g of (S)-(+)-abscisic acid (95% purity) in 10 mL of deionized water containing 50 microL of Tween 20 was prepared by stirring for a few minutes. Solid calcium hydroxide (74.09 g/mole, 370.5 mg) was added, and within a few minutes time all the abscisic acid had dissolved leaving a slightly hazy solution. Since calcium hydroxide is known to absorb carbon dioxide from the air to form calcium carbonate during storage, it was assumed that the cloudiness was due to calcium carbonate, insoluble in water at neutral pH. Potassium sorbate (63 mg) was added and it quickly dissolved. The solution was transferred to a graduated cylinder and made up to 25 mL volume by addition of deionized water, giving a 10% by weight solution of the hemicalcium salt of abscisic acid in water. The solution was filtered before transfer to a bottle for storage.

A 10% abscisic acid by weight solution in water as the hemicalcium salt comprising a naturally-occurring preservative was prepared.

Example 11

Preparation of an Aqueous Solution Composition Comprising Both Ammonium and Potassium Salts of (S)-(+)-Abscisic Acid (S)-(+)-Abscisic acid (2.64 g of 95% purity) was suspended in 15 mL of deionized water containing 50 mg of Tween 20. One quarter of the theoretical amount of potassium hydroxide (250 microL of 10.0 molar aqueous solution) was added. The remainder of the neutralization was then carried out with concentrated aqueous ammonia solution, to give a clear solution of pH 7.1. Preservative (63 mg of potassium sorbate) was added, and it quickly dissolved. The solution was made up to 25 mL final volume to give a 10% by weight aqueous composition of abscisic acid as a mixture of the ammonium and potassium salts.

A 10% aqueous solution composition comprising both ammonium and potassium salts of (S)-(+)-Abscisic acid such that the weight ratio of nitrogen to potassium is approximately 1:1, having utility per se as a foliar fertilizer in addition to its utility for applying a treatment of (S)-(+)-Abscisic acid to a plant was prepared.

Example 12

Preparation of an Aqueous Solution Composition Comprising the Trimethylammonium Salt of (S)-(+)-Abscisic Acid (S)-(+)-Abscisic acid (2.64 g of 95% purity) was suspended in 15 mL of deionized water containing 50 mg of Tween 20. An aqueous solution of trimethylamine (1.5 mL of 6.6M concentration) was added, which caused most of the abscisic acid to dissolve. The remainder of the neutralization was then carried out by careful dropwise addition of the aqueous trimethylamine, to give a clear solution of pH 6.8. Preservative (63 mg of potassium sorbate) was added, and it quickly dissolved. The solution was made up to 25 mL final volume to give a 10% by weight aqueous composition of abscisic acid as a trimethylammonium salt.

An aqueous solution composition comprising 10% abscisic acid by weight as the trimethylammonium salt was prepared.

Example 13

Preparation of an Aqueous Solution Composition of the Ammonium Salt of (S)-(+)-Abscisic Acid Comprising Brij 97 Surfactant A solution was prepared containing 5.0 g of Brij 97 in approximately 35 mL of water. (S)-(+)-abscisic acid (2.64 g of 95% purity) was added, followed by the theoretical amount of ammonia as the commercial concentrated aqueous solution. All of the abscisic acid quickly dissolved. The solution was made up to a final volume of 50 mL to give a concentration of 5% of abscisic acid as the ammonium salt and 10% of Brij 97 by weight.

An aqueous solution composition comprising 5% abscisic acid by weight as the ammonium salt and further comprising a high concentration of Brij 97 surfactant was prepared.

Example 14

Preparation of an Aqueous Solution Composition of the Ammonium Salt of (S)-(+)-Abscisic Acid Comprising Brij 98 Surfactant A solution was prepared containing 5.0 g of Brij 98 in approximately 20 mL of water. (S)-(+)-abscisic acid (2.64 g of 95% purity) was added, followed by the theoretical amount of ammonia as the commercial concentrated aqueous solution. All of the abscisic acid quickly dissolved. Preservative (63 mg of potassium sorbate) was added, and it quickly dissolved. The pH of the resulting clear solution was 6.92. It was made up to a final volume of 50 mL to give a concentration of 5% of abscisic acid as the ammonium salt and 10% of Brij 98 by weight.

An aqueous solution composition comprising 5% abscisic acid by weight as the ammonium salt and further comprising a high concentration of Brij 98 surfactant was prepared.

Example 15

Preparation of an Aqueous Solution Composition of the Ammonium Salt of (S)-(+)-Abscisic Acid Comprising Brij 700 Surfactant Brij 700 (5.0 g) was dissolved in 25 mL of water with the aid of heat and stirring. (S)-(+)-abscisic acid (2.64 g of 95% purity) was added, followed by the theoretical amount of ammonia as the commercial concentrated aqueous solution. All of the abscisic acid quickly dissolved. Antimicrobial preservative (63 mg of potassium sorbate) was added, and it quickly dissolved. The resulting solution was made up to 50 mL by addition of deionized water.

An aqueous solution composition comprising 5% abscisic acid by weight as the ammonium salt and further comprising a high concentration of Brij 700 surfactant was prepared.

Example 16

Preparation of an Aqueous Solution Composition of the Ammonium Salt of (S)-(+)-Abscisic Acid Comprising a High Concentration of Both Brij 98 and Tween 20 Surfactants A solution containing 5.0 g of Tween 20 and 5.0 g of Brij 98 in 15 mL of water was prepared with the aid of gentle heating. (S)-(+)-Abscisic acid (5.28 g of 95% purity) and a further 10 mL of water was added. After stirring for a few minutes to suspend the abscisic acid, the theoretical amount of ammonia was added in the form of the commercial concentrated aqueous solution. Stirring for several minutes gave a homogeneous solution. Potassium sorbate (125 mg) was added as an antimicrobial preservative and stirred to dissolve. The solution was transferred to a graduated cylinder and made up to a final volume of 50 mL with deionized water, to give an aqueous composition containing 10% abscisic acid as the ammonium salt, 10% Tween 20 and 10% Brij 98 by weight.

An aqueous solution composition comprising 10% abscisic acid by weight as the ammonium salt and further comprising a high concentration of both Brij 98 and Tween 20 surfactants was prepared.

Example 17

Preparation of an Aqueous Solution Composition of the Triethanolamine Salt of (S)-(+)-Abscisic Acid Comprising a High Concentration of Brij 98 Surfactant To a solution of 50 mg Tween 20 in 10 mL of water was added 2.64 g of (S)-(+)-abscisic acid (10 mmoles of 95% purity). Triethanolamine (1.33 mL, 10 mmoles) was added dropwise with good stirring, resulting in a clear, homogeneous solution. This solution was heated to 55° C., and Brij 98, liquified by warming in a 55° C. oven, was added. After stirring to achieve a homogeneous solution, the mixture was diluted with additional water to a final volume of 25 mL.

An aqueous solution composition comprising 10% abscisic acid by weight as the triethanolamine salt and further comprising 20% by weight Brij 98 as a performance-enhancing additive was prepared.

Example 18

Preparation of an Aqueous Solution Composition of the Ammonium Salt of (S)-(+)-Abscisic Acid Comprising Ammonium Nitrate To a solution of 50 mg Tween 20 in 8 mL of water was added 2.64 g of (S)-(+)-abscisic acid (10 mmoles of 95% purity). Addition of the theoretical amount of concentrated aqueous ammonia and stirring briefly brought all the abscisic acid into solution. Ammonium nitrate (8.00 g, 100 mmoles) was added, and it dissolved within a few minutes. Potassium sorbate (63 mg) was added as an antimicrobial preservative, and it dissolved within a few minutes. The solution was made up to a final volume of 25 mL by addition of deionized water.

An aqueous solution composition comprising 10% abscisic acid by weight as the ammonium salt and further comprising 32% by weight ammonium nitrate as a performance-enhancing additive was prepared.

Example 19

Preparation of an Aqueous Solution Composition of the Ammonium Salt of (S)-(+)-Abscisic Acid Comprising Magnesium Nitrate A solution was prepared by dissolving 25.6 g of magnesium nitrate hexahydrate in 15 mL deionized water. Tween 20 (50 mg) was added, followed by 2.64 g of (S)-(+)-abscisic acid (10 mmoles of 95% purity). Addition of the theoretical amount of concentrated aqueous ammonia diluted with 5 mL of water and stirring briefly brought all the abscisic acid into solution. The mixture was made up to 50 mL with deionized water and filtered. Analysis of the solution by HPLC showed 5.0% of (S)-(+)-abscisic acid.

An aqueous solution composition comprising 5% abscisic acid by weight as the ammonium salt and further comprising 51% by weight magnesium nitrate as a performance-enhancing additive was prepared.

Example 20

Preparation of an Aqueous Solution Composition of the Ammonium Salt of (S)-(+)-Abscisic Acid Comprising Ammonium Acetate (S)-(+)-abscisic acid (2.64 g, 10 mmoles of 95% purity) was suspended in a solution of 50 mg Tween 20 in 8 mL water and stirred while adding 10 mmoles of concentrated aqueous ammonia. All the abscisic acid dissolved to give a clear solution. Ammonium acetate (7.71 g, 100 mmol) was added and dissolved. The solution was made up to a final volume of 20 mL by addition of water.

An aqueous solution composition comprising 12.5% (S)-(+)-abscisic acid by weight as the ammonium salt and further comprising 38.5% by weight ammonium acetate as a performance-enhancing additive was prepared.

Example 21

Preparation of an Aqueous Solution Composition of the Ammonium Salt of (S)-(+)-Abscisic Acid Comprising Both Ammonium Nitrate and Urea A solution of ammonium nitrate (8.00 g, 100 mmoles) and urea (6.01 g, 100 mmoles) was prepared in 7 mL of water. Tween 20 (50 mg) was added, followed by 2.64 g of (S)-(+)-abscisic acid (10 mmoles of 95% purity). The abscisic acid was dissolved by addition of the theoretical amount of concentrated aqueous ammonia plus 2 mL more deionized water. The solution was made up to 25 mL volume by addition of deionized water and filtered.

An aqueous solution composition comprising 10% abscisic acid by weight as the ammonium salt and further comprising 32% by weight ammonium nitrate plus 24% by weight of urea as performance-enhancing additives was prepared.

Example 22

Preparation of an Aqueous Solution Composition of the Ammonium Salt of (S)-(+)-Abscisic Acid Comprising Both Ammonium Nitrate and Calcium Chloride A solution of calcium chloride dihydrate (14.7 g, 100 mmoles) was prepared in 10 mL of water. Tween 20 (50 mg) was added, followed by 2.64 g of (S)-(+)-abscisic acid (10 mmoles of 95% purity). Addition of the theoretical amount of concentrated aqueous ammonia produced a gummy mixture. Addition of ca. 30 mL additional deionized water and stirring overnight finally gave a clear solution. Ammonium nitrate (8.00 g, 100 mmoles) was added, and it dissolved easily. The volume of the final solution was measured to be 67 mL, corresponding to 3.7% (S)-(+)-abscisic acid by weight to volume.

An aqueous solution composition comprising 3.7% abscisic acid by weight as the ammonium salt and further comprising 11.9% by weight ammonium nitrate plus 21.9% calcium chloride dihydrate as performance-enhancing additives was prepared.

Example 23

Preparation of an Aqueous Solution Composition of the Ammonium Salt of (S)-(+)-Abscisic Acid Comprising Brij 98 Surfactant and Urea A solution of Brij 98 (5.0 g) was prepared in 10 mL warm water. Adding 2.64 g of (S)-(+)-abscisic acid (10 mmoles of 95% purity) and stirring quickly produced a milky suspension. Adding the theoretical amount of concentrated aqueous ammonia caused the abscisic acid to dissolve quickly. Urea (6.01 g, 100 mmoles) dissolved quickly when added. The solution was made up to a final volume of 25 mL by addition of deionized water.

An aqueous solution composition comprising 10% abscisic acid by weight as the ammonium salt and further comprising both 20% by weight Brij 98 and 24% urea as performance enhancing additives was prepared.

Example 24

Preparation of an Aqueous Solution Composition of the Ammonium Salt of (S)-(+)-Abscisic Acid Comprising Magnesium Nitrate and Tween 20

Tween 20 (5 grams) and magnesium nitrate hexahydrate (25.6 g, 100 mmoles) were dissolved in 20 mL water. (S)-(+)-Abscisic acid (2.64 g, 10 mmoles of 95% purity) was added. Further addition of 10 mmoles of concentrated ammonia with stirring caused all the solid to dissolve. The solution was made up to 50 mL by addition of a small volume of water.

An aqueous solution composition comprising 5% (S)-(+)-abscisic acid by weight as the ammonium salt and further comprising 51% by weight magnesium nitrate hexahydrate and 10% by weight Tween 20 as performance-enhancing additives was prepared.

Example 25

Preparation of an Aqueous Solution Composition of the Ammonium Salt of (S)-(+)-Abscisic Acid Comprising Magnesium Nitrate and Urea (S)-(+)-abscisic acid (2.64 g, 10 mmoles) was suspended in a solution of 50 mg Tween 20 in 10 mL water. Addition of 10 mmoles of concentrated ammonia solution with stirring caused all the abscisic acid to dissolve, forming a homogeneous solution. Magnesium nitrate hexahydrate (25.6 g, 100 mmoles) was added and dissolved. Urea (6.01 g, 100 mmoles) was added and dissolved. The solution was then diluted to 38 mL in a graduated cylinder and stored in a brown bottle.

An aqueous solution composition comprising 6.5% (S)-(+)-abscisic acid by weight as the ammonium salt and further comprising 67% by weight magnesium nitrate hexahydrate and 15.8% by weight urea as performance-enhancing additives was prepared.

Example 26

Preparation of an Aqueous Solution Composition of the Ammonium Salt of (S)-(+)-Abscisic Acid Comprising Tween 20, Calcium Chloride and Urea A composition was prepared from 5.0 g Tween 20, 14.7 g calcium chloride dihydrate, 6.0 g urea 250 mg potassium sorbate and the ammonium salt prepared from 2.64 g of (S)-(+)-abscisic acid (95% purity). This complex mixture did not become homogeneous until diluted to nearly 100 mL, so the final volume was adjusted to exactly 100 mL, corresponding to 2.5% (S)-(+)-abscisic acid.

An aqueous solution composition comprising 2.5% (S)-(+)-abscisic acid by weight as the ammonium salt and further comprising 5% by weight Tween 20 and 14.7% by weight calcium chloride dihydrate plus 6.0% by weight urea as performance-enhancing additives was prepared.

Example 27

Preparation of an Aqueous Solution Composition of the Ammonium Salt of (S)-(+)-Abscisic Acid Comprising Sodium Erythorbate Antioxidant A solution of the ammonium salt of (S)-(+)-abscisic acid comprising 0.25% potassium sorbate prepared as in example 5.A. above (399.2 grams) was stirred with 0.80 grams of sodium erythorbate until all the solid had dissolved. The solution was stored in a brown bottle.

An aqueous solution composition comprising 10% (S)-(+)-abscisic acid by weight as the ammonium salt and further comprising 0.25% by weight potassium sorbate and 0.2% by weight sodium erythorbate as stability enhancing additives was prepared.

Example 28

Preparation of an Aqueous Solution Composition of the Ammonium Salt of (S)-(+)-Abscisic Acid Comprising Ascorbyl Phosphate Antioxidant A solution of the ammonium salt of (S)-(+)-abscisic acid comprising 0.25% potassium sorbate prepared as in example 5.A. above (399.2 grams) was stirred with 0.80 grams of ascorbyl phosphate until all the solid had dissolved. The solution was stored in a brown bottle.

An aqueous solution composition comprising 10% (S)-(+)-abscisic acid by weight as the ammonium salt and further comprising 0.25% by weight potassium sorbate and 0.2% by weight ascorbyl phosphate as stability enhancing additives was prepared.

Example 29

Preparation of an Aqueous Solution Composition of the Ammonium Salt of (S)-(+)-Abscisic Acid Comprising Propyl Gallate Antioxidant A solution of the ammonium salt of (S)-(+)-abscisic acid comprising 0.25% potassium sorbate prepared as in example 5.A. above (99.5 grams) was stirred with 0.50 grams of propyl gallate until all the added material had dissolved. The solution was passed through a 325-mesh screen and stored in a brown bottle.

An aqueous solution composition comprising 10% (S)-(+)-abscisic acid by weight as the ammonium salt and further comprising 0.25% by weight potassium sorbate and 0.25% by weight propyl gallate as stability enhancing additives was prepared.

Example 30

Preparation of an Aqueous Solution Composition of the Ammonium Salt of (S)-(+)-Abscisic Acid Comprising Sodium Sulfite Antioxidant A solution of the ammonium salt of (S)-(+)-abscisic acid comprising 0.25% potassium sorbate prepared as in example 5.A. above (99.75 grams) was stirred with 0.25 grams of sodium sulfite until all the added solid had dissolved. The solution was passed through a 325-mesh screen and stored in a brown bottle.

An aqueous solution composition comprising 10% (S)-(+)-abscisic acid by weight as the ammonium salt and further comprising 0.25% by weight potassium sorbate and 0.25% by weight sodium sulfite as stability enhancing additives was prepared.

Example 31

Preparation of an Aqueous Solution Composition of the Ammonium Salt of (S)-(+)-Abscisic Acid Comprising Trisodium Citrate A solution of the ammonium salt of (S)-(+)-abscisic acid comprising 0.25% potassium sorbate prepared as in example 5.A. above (99.5 grams) was stirred with 0.50 grams of trisodium citrate until all the added material had dissolved. The solution was passed through a 325-mesh screen and stored in a brown bottle.

An aqueous solution composition comprising 10% (S)-(+)-abscisic acid by weight as the ammonium salt and further comprising 0.25% by weight potassium sorbate and 0.5% by weight sodium citrate as stability enhancing additives was prepared.

Example 32

Preparation of an Aqueous Solution Composition of the Potassium Salt of (S)-(+)-Abscisic Acid Comprising Propyl Gallate Antioxidant A solution of the potassium salt of (S)-(+)-abscisic acid comprising 0.25% potassium sorbate prepared as in example 6.A. above (99.5 grams) was stirred with 0.50 grams of propyl gallate until all the added material had dissolved. The solution was passed through a 325-mesh screen and stored in a brown bottle.

An aqueous solution composition comprising 10% (S)-(+)-abscisic acid by weight as the potassium salt and further comprising 0.25% by weight potassium sorbate and 0.5% by weight propyl gallate as stability enhancing additives was prepared.

Example 33

Preparation of an Aqueous Solution Composition of the Potassium Salt of (S)-(+)-Abscisic Acid Comprising Sodium Sulfite Antioxidant A solution of the potassium salt of (S)-(+)-abscisic acid comprising 0.25% potassium sorbate prepared as in example 6.A. above (99.75 grams) was stirred with 0.25 grams of sodium sulfite until all the added material had dissolved. The solution was passed through a 325-mesh screen and stored in a brown bottle.

An aqueous solution composition comprising 10% (S)-(+)-abscisic acid by weight as the potassium salt and further comprising 0.25% by weight potassium sorbate and 0.25% by weight sodium sulfite as stability enhancing additives was prepared.

Example 34

Preparation of an Aqueous Solution Composition of the Potassium Salt of (S)-(+)-Abscisic Acid Comprising Trisodium Citrate A solution of the potassium salt of (S)-(+)-abscisic acid comprising 0.25% potassium sorbate prepared as in example 6.A. above (99.5 grams) was stirred with 0.50 grams of trisodium citrate until all the added material had dissolved. The solution was passed through a 325-mesh screen and stored in a brown bottle.

An aqueous solution composition comprising 10% (S)-(+)-abscisic acid by weight as the potassium salt and further comprising 0.25% by weight potassium sorbate and 0.5% by weight trisodium citrate as stability enhancing additives was prepared.

Example 35

Preparation of an Aqueous Solution Composition of the Ammonium Salt of (S)-(+)-Abscisic Acid Comprising Trisodium Citrate and Sodium Sulfite Water (1609 g) was used to make a solution containing 2.0 g Tween 20, 5.0 g potassium sorbate, 5.0 g sodium sulfite and 10 g trisodium citrate. Adding 110 g of (S)-(+)-abscisic acid (95% purity) followed by 20.7 g of concentrated aqueous ammonia allowed most of the abscisic acid to dissolve. After adding a further 101 g of (S)-(+)-abscisic acid and 21.6 g of concentrated ammonia, again most of the abscisic acid was dissolved. Cautious addition of 6.8 g more ammonia solution was required to bring all solid into solution. Water was added to make a total batch weight of 2000 g, and the solution was passed through a 500-mesh screen. The final pH was 6.62.

An aqueous solution composition comprising 10% (S)-(+)-abscisic acid by weight as the ammonium salt and further comprising 0.25% by weight potassium sorbate, 0.25% sodium sulfite and 0.5% by weight trisodium citrate as stability enhancing additives was prepared.

Example 36

Preparation of an Aqueous Solution Composition of the Potassium Salt of (S)-(+)-Abscisic Acid Comprising Trisodium Citrate and Sodium Sulfite Water (800 g) was used to make a solution containing 1.0 g Tween 20, 2.5 g potassium sorbate, 1.0 g sodium sulfite and 5.0 g trisodium citrate. Adding 55 g of (S)-(+)-abscisic acid (95% purity) followed by 23 g of 45% aqueous potassium hydroxide allowed most of the abscisic acid to dissolve. After adding a further 50 g of (S)-(+)-abscisic acid and 19 g of 45% aqueous potassium hydroxide, again most of the abscisic acid was dissolved. Cautious addition of 2.0 g of 45% aqueous potassium hydroxide was required to bring all solid into solution. Water was added to make a total batch weight of 1000 g, and the solution was passed through a 500-mesh screen. The final pH was 6.60.

An aqueous solution composition comprising 10% (S)-(+)-abscisic acid by weight as the potassium salt and further comprising 0.25% by weight potassium sorbate, 0.1% sodium sulfite and 0.5% by weight trisodium citrate as stability enhancing additives was prepared.

Preparation of plant specimens for use in the treatment studies of the EXAMPLES that follow was carried out as follows. Tomato (variety: Rutgers) seeds were sown in an 18-cell flat filled with Promix PGX (available from Premier Horticulture Inc., Quakertown Pa.) and grown for 3 weeks to allow for germination and initial growth. Plants were then transplanted into pots (18 cm in diameter and 18 cm in height), filled with Promix BX (available from Premier Horticulture Inc., Quakertown Pa.), and grown for one or two more weeks before treatment, depending on temperature and available light. Plants received daily irrigation and weekly fertilizer (1 g/L all purpose fertilizer 20-20-20, available from The Scotts Company, Marysville, Ohio).

All treatment solutions were made up with distilled water. The (S)-(+)-abscisic acid (95% active ingredient) is available from Lomon BioTechnology Co., Ltd. (Shichuan, China). Twenty L of a 250 ppm solution of (S)-(+)-abscisic acid was prepared and stored in the dark at 20-25° C. This same 250-ppm (S)-(+)-abscisic acid solution was used as a control for all studies to eliminate the possibility of applying an incorrect concentration.

All experiments were conducted using a randomized complete block experimental design. Solutions of (S)-(+)-abscisic acid and blank treatments (plain water) were applied by spray to the aerial parts of the tomato plants at the rate of 20 mL per 6 plants. Plants were then placed in a transparent chamber with humidity controlled within the range of 40 to 60% relative humidity. Leaf transpiration rates were measured at 1, 2 and 3 days after treatment. Measurements were conducted using a LI-1600 Steady State Porometer (LI-Cor, Lincoln, Nebr.). Each day the transpiration rate of the plants of each treatment group was normalized to a percentage of the transpiration rate of untreated plants (plants sprayed with water only) in order to control for day-to-day variability in plant status caused by changes of environmental conditions such as light intensity and temperature. Data of each plant was also averaged over a 3-day period to balance the short term and long term effect of (S)-(+)-abscisic acid on tomato leaf transpiration as well as to reduce experimental variability.

Example 37

The effect of (S)-(+)-abscisic acid, in comparison with the effects of the abscisic acid organic amine salts of the present invention, as prepared in the Examples 1, 2 and 3 was studied in an assay measuring tomato leaf transpiration rate (Table 1). The aqueous solution compositions of the Examples were each diluted with water to a final application concentration of 250 ppm (based on (S)-(+)-abscisic acid content) to match the (S)-(+)-abscisic acid (non-salt) standard treatment.

TABLE 1

Effect of (S)-(+)-abscisic acid vs. organic amine salts of (S)-(+)-abscisic acid on tomato leaf transpiration

| Treatment | Transpiration rate (% of control) Days after treatment | | | |
|---|---|---|---|---|
| | 1 | 2 | 3 | 3-Day Average |
| Water Control | 100.00 | 100.00 | 100.00 | 100.00 |
| 250 ppm (S)-(+)-abscisic acid | 75.59 | 89.83 | 95.63 | 87.02 |
| 250 ppm (S)-(+)-abscisic acid salt composition of Example 3 | 76.60 | 80.86 | 96.37 | 84.61 |
| 250 ppm (S)-(+)-abscisic acid salt composition of Example 1 | 60.03 | 73.91 | 71.72 | 68.55 |
| 250 ppm (S)-(+)-abscisic acid salt composition of Example 2 | 67.06 | 83.34 | 94.23 | 81.54 |

Thus it has been demonstrated that the organic amine salt compositions of (S)-(+)-abscisic acid of the present invention are at least as efficacious biologically as (S)-(+)-abscisic acid itself.

Example 38

The effect of (S)-(+)-abscisic acid as compared to the alkali metal salts of (S)-(+)-abscisic acid of Examples 7 and 8 on tomato leaf transpiration rate was studied (Table 2).

TABLE 2

Effect of (S)-(+)-abscisic acid vs. different (S)-(+)-abscisic acid alkali metal salts on tomato leaf transpiration

| | Transpiration rate (% of control) Days after treatment | | | |
|---|---|---|---|---|
| Treatment | 1 | 2 | 3 | 3-Day Average |
| Water Control | 100.00 | 100.00 | 100.00 | 100.00 |
| 250 ppm (S)-(+)-abscisic acid | 75.59 | 89.83 | 95.63 | 87.02 |
| 250 ppm (S)-(+)-abscisic acid salt composition of Example 8 | 70.54 | 77.03 | 84.14 | 77.24 |
| 250 ppm (S)-(+)-abscisic acid salt composition of Example 7 | 82.55 | 83.52 | 91.41 | 85.83 |

Thus it has been demonstrated that the alkali metal salt compositions of (S)-(+)-abscisic acid of sodium and lithium of the present invention are at least as efficacious biologically as (S)-(+)-abscisic acid itself.

Example 39

The effect of (S)-(+)-abscisic vs. the (S)-(+)-abscisic acid salt compositions of Example 5, Example 6, Example 9 and Example 10 on tomato leaf transpiration rate was studied (Table 3).

TABLE 3

Effect of different (S)-(+)-abscisic salts on tomato transpiration inhibition

| | Transpiration rate (% of control) Days after treatment | | | |
|---|---|---|---|---|
| Treatment | 1 | 2 | 3 | 3-Day Average |
| Water Control | 100.00 | 100.00 | 100.00 | 100.00 |
| 250 ppm ABA | 72.66 | 76.18 | 93.50 | 80.78 |
| 250 ppm (S)-(+)-abscisic acid salt composition of Example 5 | 68.07 | 73.08 | 83.57 | 74.90 |
| 250 ppm (S)-(+)-abscisic acid salt composition of Example 6 | 58.21 | 80.41 | 92.17 | 76.93 |
| 250 ppm (S)-(+)-abscisic acid salt composition of Example 9 | 57.41 | 67.60 | 75.66 | 66.89 |
| 250 ppm (S)-(+)-abscisic acid salt composition of Example 10 | 83.43 | 69.71 | 92.08 | 81.74 |

Thus it has been demonstrated that the alkali metal and alkaline earth salt compositions of (S)-(+)-abscisic acid of potassium, magnesium and calcium of the present invention are at least as efficacious biologically as (S)-(+)-abscisic acid itself.

Example 40

The effect of (S)-(+)-abscisic vs. the (S)-(+)-abscisic acid salt compositions of Example 5, Example 14, Example 16, Example 26 and Example 11 on tomato leaf transpiration rate was studied (Table 4).

TABLE 4

Effect of different additives or salt combinations on (S)-(+)-abscisic acid ammonium salt performance for tomato leaf transpiration inhibition

| | Transpiration rate (% of control) Days after treatment | | | |
|---|---|---|---|---|
| Treatment | 1 | 2 | 3 | 3-Day Average |
| Water Control | 100.00 | 100.00 | 100.00 | 100.00 |
| 250 ppm (S)-(+)-abscisic acid | 75.30 | 83.65 | 90.68 | 83.21 |
| 250 ppm (S)-(+)-abscisic acid salt composition of Example 5 | 73.53 | 75.40 | 93.33 | 80.75 |
| 250 ppm (S)-(+)-abscisic acid salt composition of Example 14 | 21.08 | 33.96 | 68.31 | 41.12 |
| 250 ppm (S)-(+)-abscisic acid salt composition of Example 16 | 43.65 | 54.20 | 69.39 | 55.75 |
| 250 ppm (S)-(+)-abscisic acid salt composition of Example 26 | 48.90 | 59.14 | 87.71 | 65.25 |
| 250 ppm (S)-(+)-abscisic acid salt composition of Example 11 | 71.78 | 73.21 | 91.31 | 78.77 |

Thus it has been demonstrated that various additives to the ammonium salt composition of (S)-(+)-abscisic acid of the present invention can increase the biological activity substantially (entries for compositions of Examples 14, 16 and 26). It has also been demonstrated that the composition of Example 11, comprising both ammonium and potassium salts, such that the weight ratio of nitrogen to potassium is approximately 1:1, is at least as efficacious in reducing transpiration as (S)-(+)-abscisic acid or the (S)-(+)-abscisic acid ammonium salt of the present invention.

Example 41

The effect of (S)-(+)-abscisic acid, vs. the (S)-(+)-abscisic acid salt compositions of Example 5, Example 15, Example 18, Example 19, Example 21, Example 22 and Example 23 on tomato leaf transpiration rate was studied, with the results presented in Table 5.

TABLE 5

Effect of different added components on improving (S)-(+)-abscisic acid ammonium salt performance for tomato leaf transpiration inhibition

| | Transpiration rate (% of control) Days after treatment | | | |
|---|---|---|---|---|
| Treatment | 1 | 2 | 3 | 3-Day Average |
| Water Control | 100.00 | 100.00 | 100.00 | 100.00 |
| 250 ppm (S)-(+)-abscisic acid | 59.35 | 71.02 | 76.62 | 69.00 |
| 250 ppm (S)-(+)-abscisic acid salt of Example 5 | 57.45 | 67.13 | 77.97 | 67.52 |
| 250 ppm (S)-(+)-abscisic acid salt composition of Example 15 | 19.13 | 37.05 | 46.60 | 34.26 |
| 250 ppm (S)-(+)-abscisic acid salt composition of Example 19 | 33.75 | 42.49 | 46.87 | 41.04 |
| 250 ppm (S)-(+)-abscisic acid salt composition of Example 18 | 42.61 | 61.20 | 52.45 | 52.09 |
| 250 ppm (S)-(+)-abscisic acid salt composition of Example 23 | 14.94 | 27.70 | 28.08 | 23.57 |
| 250 ppm (S)-(+)-abscisic acid salt composition of Example 21 | 26.80 | 47.91 | 53.20 | 42.64 |
| 250 ppm (S)-(+)-abscisic acid salt composition of Example 22 | 46.00 | 62.59 | 70.80 | 59.79 |

Thus it has been demonstrated that various additives to the ammonium salt composition of (S)-(+)-abscisic acid of the present invention can increase the biological activity substantially (entries for compositions of Examples 15, 18, 19, 21, 22 and 23).

Example 42

The effect of (S)-(+)-abscisic acid vs. the (S)-(+)-abscisic acid salt compositions of Example 5 and Example 19 on tomato leaf transpiration rate was studied (Table 6).

TABLE 6

Effect of ABA ammonium salt ammonium salt with or without ammonium acetate on tomato leaf transpiration

| Treatment | Transpiration rate (% of control) Days after treatment | | | |
|---|---|---|---|---|
| | 1 | 2 | 3 | 3-Day Average |
| Water Control | 100.00 | 100.00 | 100.00 | 100.00 |
| 250 ppm (S)-(+)-abscisic acid ammonium salt composition of Example 5 | 75.63 | 78.14 | 88.12 | 80.63 |
| 250 ppm (S)-(+)-abscisic acid ammonium salt composition of Example 19 comprising ammonium acetate | 59.85 | 59.48 | 84.63 | 67.99 |

Thus it has been demonstrated that the ammonium salt composition of (S)-(+)-abscisic acid of the present invention comprising a high concentration of ammonium acetate, as described in Example 19, is much more efficacious biologically than (S)-(+)-abscisic acid ammonium salt itself, the composition of Example 5.

Example 43

The effect of (S)-(+)-abscisic acid vs. the (S)-(+)-abscisic acid triethanolamine salt composition of Example 16, comprising a high concentration of Brij 98, on tomato leaf transpiration rate was studied (Table 7).

TABLE 7

Effect of (S)-(+)-abscisic acid vs. (S)-(+)-abscisic acid triethanolamine salt comprising Brij 98 on tomato leaf transpiration

| Treatment | Transpiration rate (% of control) Days after treatment | | | |
|---|---|---|---|---|
| | 1 | 2 | 3 | 3-Day Average |
| Water Control | 100.00 | 100.00 | 100.00 | 100.00 |
| 250 ppm (S)-(+)-abscisic acid | 71.16 | 75.23 | 88.25 | 78.21 |
| 250 ppm (S)-(+)-abscisic acid salt composition of Example 16 | 28.56 | 27.63 | 38.79 | 31.66 |

Thus it has been demonstrated that the triethanolamine salt composition of (S)-(+)-abscisic acid of the present invention comprising a high concentration Brij 98, as described in Example 16, is much more efficacious biologically than (S)-(+)-abscisic acid itself is.

Example 44

Relative Efficacy of the (S)-(+)-Abscisic Acid Ammonium Salt of the Present Invention vs. the Prior Art (R,S)-(±)-Abscisic Acid Ammonium Salt Treatments with (R,S)-(±)-abscisic acid as the ammonium salt at 250 or 500 ppm were compared to treatments with (S)-(+)-abscisic acid ammonium salt at 125, 250 and 500 ppm on their performance for transpiration inhibition with the results shown in Table 8.

TABLE 8

Comparison the inhibitory effect on tomato leaf transpiration of (S)-(+)-abscisic acid ammonium salt vs. (R,S)-(±)-abscisic acid ammonium salt

| Treatment | Transpiration rate (% of control) Days after treatment | | | |
|---|---|---|---|---|
| | 1 | 2 | 3 | 3-Day Average |
| Water Control | 100.00 | 100.00 | 100.00 | 100.00 |
| 250 ppm ABA | 71.16 | 75.23 | 88.25 | 78.21 |
| 125 ppm (S)-(+)-abscisic acid ammonium salt composition of Example 5 | 89.77 | 89.66 | 95.79 | 91.74 |
| 250 ppm (S)-(+)-abscisic acid ammonium salt composition of Example 5 | 75.63 | 78.14 | 88.12 | 80.63 |
| 500 ppm (S)-(+)-abscisic acid ammonium salt composition of Example 5 | 62.58 | 64.23 | 80.02 | 68.94 |
| 250 ppm (R,S)-(±)-abscisic acid as the ammonium salt | 90.26 | 87.73 | 94.86 | 90.95 |
| 500 ppm (R,S)-(±)-abscisic acid as the ammonium salt | 77.53 | 76.20 | 89.36 | 81.03 |

From the results presented, it can be seen that application of 125 ppm of (S)-(+)-abscisic acid ammonium salt produces a reduction in transpiration equal to that produced by application of 250 ppm of (R,S)-(±)-abscisic acid ammonium salt. It is also apparent that application of 250 ppm of (S)-(+)-abscisic acid ammonium salt produces a reduction in transpiration equal to that produced by application of 500 ppm of (R,S)-(±)-abscisic acid ammonium salt.

Accordingly, it has been demonstrated that the (S)-(+)-abscisic acid salts of the present invention are biologically active at one-half the total dose rate of the prior art salts of racemic (R,S)-(±)-abscisic acid.

Example 45

Relative Phytotoxicity of (S)-(+)-Abscisic Acid Ammonium Salt of the Present Invention vs. the Prior Art (R,S)-(±)-Abscisic Acid Ammonium Salt Phytotoxicity is defined as damage to a plant caused by treatment with an externally applied chemical substance. Phytotoxicity caused by application of an agricultural chemical is considered highly undesirable (except in the case of herbicides). To test the relative safety of the compositions of the present invention, comprising an ammonium salt of (S)-(+)-abscisic acid, as compared to compositions of the prior art, comprising an ammonium salt of (R,S)-(±)-abscisic acid, plants were treated with solutions containing two different concentrations of the (S)-(+)-abscisic acid or with solutions containing (R,S)-(±)-abscisic acid at concentrations in which either the total concentration of (R,S)-(±)-abscisic acid was equal to the higher concentration of (S)-(+)-abscisic acid or in which the concentration of (S)-(+)-abscisic acid contained in the (R,S)-(±)-abscisic acid was equal to the higher treatment concentration of the pure (S)-(+)-abscisic acid.

California Blackeye Pea (cowpea) seed was planted into 18 cell flats filled with Promix PGX in a greenhouse. When the plants had grown to a point where the monofoliate leaves were fully expanded and the first trifoliate leaves were emerging (18 days after planting) the plants were sprayed with 1.5 ml of treatment solution. After treatment the plants were held in the greenhouse and evaluated for damage to the monofoliate leaves and also for growth of the trifoliate leaves. The percentage of the monofoliate leaf area that was damaged was estimated three days after treatment, and monofoliate leaf abscission and trifoliate leaf development were determined on the fifth day after treatment. The results are summarized in Table 9.

TABLE 9

The effect of Foliar Application of (S)-(+)-abscisic acid ammonium salt vs. racemic (R,S)-(±)-abscisic acid salt on Phytotoxicity and Growth of California Blackeye Pea

| Treatment | (S)-(+)-Enantiomer content | % Leaf Area Damaged 3 days after treatment | Average Number of Abscised Monofoliate Leaves 5 days after treatment | Average Number of New Trifoliate Leaves 5 days after treatment |
|---|---|---|---|---|
| Water only | | 0 | 0.0 | 1.8 |
| 3125 ppm (S)-(+)-abscisic acid salt of Example 5 | 3125 ppm | 72 | 0.2 | 1.3 |
| 6250 ppm (S)-(+)-abscisic acid salt of Example 5 | 6250 ppm | 98 | 1.5 | 0.8 |
| 6250 ppm (R,S)-(±)-abscisic acid as the ammonium salt | 3125 ppm | 97 | 1.7 | 0.0 |
| 12500 ppm (R,S)-(±)-abscisic acid as the ammonium salt | 6250 ppm | 100 | 2.0 | 0.0 |

Treating cowpea with (S)-(+)-abscisic acid in an (S)-(+)-only treatment vs. an (R,S)-(±)-treatment produced different degrees of phytotoxicity as demonstrated most prominently in measures of the average number of monofoliate leaves lost per plant and in the rate of development of new trifoliate leaves. Plants to which the (R,S)-(±)-abscisic acid treatment was applied exhibited more phytotoxicity than plants treated with the (S)-(+)-abscisic acid only solutions, whether compared at an equal total material dose or at an equal dose of (S)-(+)-enantiomer abscisic acid content.

Accordingly, it has surprisingly been found that the (S)-(+)-abscisic acid salt compositions of the present invention are safer to apply to plants than prior art salt compositions of (R,S)-(±)-abscisic acid.

Products sold in commerce, when intended for agricultural applications, are commonly subjected to temperature conditions outside the range normally experienced indoors and are frequently stored for extended periods in warehouses or outdoor sheds before use. Thus it is important that such agricultural formulations be stable in active ingredient composition and appearance for a year or more under ordinary room temperature conditions or for at least shorter periods at more elevated temperatures. In order to ensure adequate stability in commerce, formulations of the present invention were subjected to thermal stress testing by heating in an oven at 54° C. for two to four weeks and then assayed for changes in the concentration of the (S)-(+)-abscisic acid salt and monitored for changes in visual appearance by matching samples against a Gardner color chart and examination for possible appearance of precipitated material. Color readings of 5 or greater on the Gardner chart are considered undesirable. Color readings of freshly prepared Examples are all below 1 on the Gardner chart.

Example 46

Storage Stability Testing of the Compositions of Examples 27 and 28

Sodium erythorbate and ascorbyl phosphate are antioxidant stabilizers commonly employed in processed food products. They were incorporated into the compositions of Examples 27 and 28, respectively, as a means to achieve long-term stability of the compositions. The samples were then incubated for various periods of time in a controlled-temperature chamber held at 25° C. and observed for color degradation. The results of this test are shown in Table 10 below.

TABLE 10

Gardner Color Chart readings of (S)-(+)-abscisic acid ammonium salt compositions after incubation in 25° C. chamber for various time periods.

| | Gardner chart color of sample after incubation at 25° C. for the following periods of time: | | |
|---|---|---|---|
| Sample | One week | Two weeks | Three weeks |
| (S)-(+)-abscisic acid salt composition of Example 27. | 2 | 5 | 9.5 |
| (S)-(+)-abscisic acid salt composition of Example 28. | 1 | 2 | 2.5 |

It has thus been demonstrated that incorporation of the commonly used antioxidant stabilizing agents sodium erythorbate or ascorbyl phosphate into the compositions of the present invention does not result in good long-term color stability at typical ambient temperatures.

Example 47

Stability Stress Testing of the Compositions of Examples 5.A, 6.A, 29, 30, 31, 32, 33 and 34

Propyl gallate and sodium sulfite are antioxidant stabilizers commonly employed in agricultural pesticide products. Sodium citrate is a chelating agent that is commonly employed in food products to control microbial growth. These were incorporated into the (S)-(+)-abscisic acid ammonium salt compositions of Examples 29, 30 and 31, respectively, and into the (S)-(+)-abscisic acid potassium salt compositions of Examples 32, 33 and 34, respectively as a means to achieve long-term stability of the compositions. The samples were then incubated for various periods of time in an oven held at 54° C. and observed for color degradation. The results of this test are shown in Table 11 below.

TABLE 11

Gardner Color Chart readings and observations of (S)-(+)-abscisic acid ammonium and potassium salt compositions after incubation in 54° C. chamber for various time periods.

| Sample | Gardner chart color of sample after incubation at 54° C. for the following periods of time: | | Observations |
|---|---|---|---|
| | Two weeks | Four weeks | |
| (S)-(+)-abscisic acid salt composition of Example 5.A. | 12 | 16 | Some precipitation |
| (S)-(+)-abscisic acid salt composition of Example 6.A | 8.5 | 11 | Isolated specks |
| (S)-(+)-abscisic acid salt composition of Example 29 comprising propyl gallate | 10 | 12 | Some precipitation |
| (S)-(+)-abscisic acid salt composition of Example 30 comprising sodium sulfite | 7 | 10 | Isolated specks |
| (S)-(+)-abscisic acid salt composition of Example 31 comprising sodium citrate | 9 | 11 | Isolated specks |
| (S)-(+)-abscisic acid salt composition of Example 32 comprising propyl gallate | 4.5 | 6 | Some precipitation |
| (S)-(+)-abscisic acid salt composition of Example 33 comprising sodium sulfite | 6 | 10 | Isolated specks |
| (S)-(+)-abscisic acid salt composition of Example 34 comprising sodium citrate | 1 | 3.5 | Clear |

It has thus been demonstrated that incorporation of the commonly used antioxidant stabilizing agents propyl gallate or sodium sulfite singly into the compositions of the present invention does not result in good long-term color stability under thermal stress conditions. It has also been surprisingly demonstrated that the commonly employed chelating agent sodium citrate is able to retard substantially the development of discoloration and the appearance of precipitate in the formulation, but only for the potassium salt composition and not for the ammonium salt composition.

Example 48

Stability Stress Testing of the Compositions of Examples 5.A, 6.A, 30 and 35 are Shown in Table 12

TABLE 12

Stability stress testing of the compositions of Examples 5.A, 6.A, 30, and 35

| | Gardner chart color of sample after incubation at 54° C. for the following periods of time: | | |
|---|---|---|---|
| | Two weeks | Three weeks | Four weeks |
| (S)-(+)-abscisic acid ammonium salt composition of Example 5A | 5 | 6.5 | 10 |
| (S)-(+)-abscisic acid salt composition of Example 30 comprising sodium sulfite | 1 | 1.75 | 4.5 |
| (S)-(+)-abscisic acid salt composition of Example 35 comprising sodium sulfite and sodium citrate | <1 | 1 | 1.5 |

Thus, it has been demonstrated that color of the compositions is more stable in the compositions of the Examples 31 and 36 than in the composition of Example 5A.

The invention claimed is:

1. An aqueous composition consisting essentially of about 10 weight % of ammonium salt of (S)-(+)-abscisic acid, about 0.25 weight % potassium sorbate, about 0.10 weight % Tween 20, about 0.25 weight % sodium sulfite, about 0.50 weight % sodium citrate, and about 86.4 weight % water.

2. An aqueous composition consisting essentially of about 10 weight % of potassium salt of (S)-(+)-abscisic acid, about 0.25 weight % potassium sorbate, about 0.5 weight % sodium citrate as the color stabilizer, and about 83.8 weight % water.

3. A method of preparing the composition of claim 1 comprising combining (S)-(+)-abscisic acid with water and Tween 20, adding concentrated ammonia hydroxide, stirring the mixture, diluting the mixture with additional water, adding potassium sorbate, and adding sodium sulfite and sodium citrate.

4. A method of preparing the composition of claim 2 comprising combining (S)-(+)-abscisic acid with water and a surfactant, adding concentrated potassium hydroxide, stirring the mixture, diluting the mixture with additional water, adding potassium sorbate, and adding sodium citrate.

* * * * *